United States Patent
Barcan et al.

(10) Patent No.: US 11,186,558 B2
(45) Date of Patent: Nov. 30, 2021

(54) SYNTHETIC METHODS

(71) Applicant: GLAXOSMITHKLINE INTELLECTUAL PROPERTY (NO. 2) LIMITED, Middlesex (GB)

(72) Inventors: Gregg Barcan, Collegeville, PA (US); Jiasheng Guo, Collegeville, PA (US); Christopher W. Morgan, Collegeville, PA (US); Gheorghe D. Roiban, Stevenage (GB); Peter W. Sutton, Stevenage (GB)

(73) Assignee: GlaxoSmithKline Intellectual Property (No.2) Limited, Middlesex (GB)

( * ) Notice: Subject to any disclaimer, the term of this patent is extended or adjusted under 35 U.S.C. 154(b) by 103 days.

(21) Appl. No.: 16/305,439

(22) PCT Filed: Jun. 27, 2017

(86) PCT No.: PCT/IB2017/053839
§ 371 (c)(1),
(2) Date: Nov. 29, 2018

(87) PCT Pub. No.: WO2018/002827
PCT Pub. Date: Jan. 4, 2018

(65) Prior Publication Data
US 2020/0325110 A1 Oct. 15, 2020

Related U.S. Application Data

(60) Provisional application No. 62/411,776, filed on Oct. 24, 2016, provisional application No. 62/355,016, filed on Jun. 27, 2016.

(51) Int. Cl.
| | | |
|---|---|---|
| *C07D 281/10* | (2006.01) | |
| *C07D 303/04* | (2006.01) | |
| *C12P 17/02* | (2006.01) | |

(52) U.S. Cl.
CPC ......... *C07D 281/10* (2013.01); *C07D 303/04* (2013.01); *C12P 17/02* (2013.01); *C12Y 303/02009* (2013.01)

(58) Field of Classification Search
CPC .................................................. C07D 281/10
See application file for complete search history.

(56) References Cited

U.S. PATENT DOCUMENTS 9,834,529 B2  12/2017  Guo et al.

FOREIGN PATENT DOCUMENTS

| WO | WO 2011/137135 A1 | 11/2011 |
| WO | WO 2016/020785 A1 | 2/2016 |

OTHER PUBLICATIONS

Yulin, et al. Journal of Medicinal Chemistry, American Chemical Society, 56(12): 5094-5114 (May 16, 2013).
Bala, et al. Tetrahedron: Asymmetry, 21: 2879-2898 (2010).
Hegade, et al. Journal of Hepatology, 62: S851-S852 (2015).
J.G. van der Watt. International Journal of Pharmaceutics, 36: 51-54 (1987).
Roiban, et al., "Development of an Enzymatic Process for the Production of (R)-2-Butyl-2-ethyloxirane", Organic Process Research and Development, 2017, 21, 1302-1310.
Xue, et al., "A novel enantioselective epoxide hydrolase from Agromyces mediolanus ZJB120203: Cloning, characterization and application", Process Biochemistry, 2014, 49, 409-417.
Krenn, et al. "Bacterial epoxide hydrolases of opposite enantiopreference". Biotechnology Letters, 21: 687-690 (1999).

*Primary Examiner* — Brenda L Coleman
(74) *Attorney, Agent, or Firm* — Robert H. Brink; Scott Young; Duke M. Fitch

(57) ABSTRACT

Methods for the preparation of the following compound are disclosed.

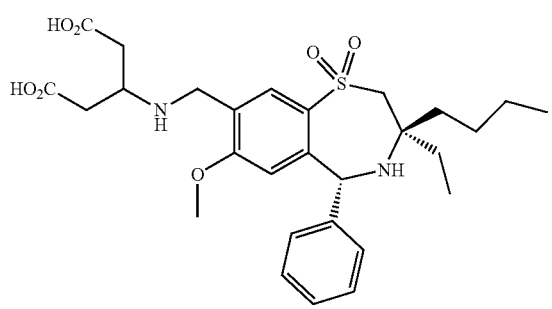

The compound can be incorporated into pharmaceutical formulations, including tablets and such tablets can be used for treating cholestatic liver diseases.

21 Claims, No Drawings

SYNTHETIC METHODS

This application is a § 371 of International Application No. PCT/IB2017/053839, filed 27 Jun. 2017, which claims the benefit of U.S. Provisional Application Nos. 62/411,776, filed 24 Oct. 2016, and 62/355,016, filed 27 Jun. 2016.

FIELD OF THE INVENTION

The present invention relates to improved synthetic methods for certain compounds that are useful in the treatment and prevention of metabolic disorders, including diabetes mellitus (Type I and Type II), obesity, and for the prophylaxix and/or treatment of a liver disease.

BACKGROUND OF THE INVENTION

Patent publication WO 2011/137,135 dislcoses, among other compounds, the following IBAT inhibitor compound. This patent publication also discloses methods of synthesis of the compound.

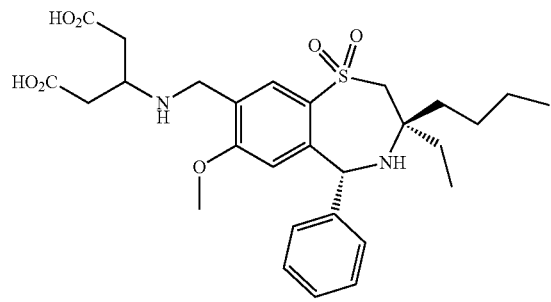 [SMILES: CCCC[C@]1(CC)CS(=O)(=O)c2cc(CNC(CC(=O)O)CC(=O)O)c(OC)cc2[C@@H](c2ccccc2)N1]

The preparation of the above compound is also disclosed in J. Med. Chem, Vol 56, pp 5094-5114 (2013) and in J. Org. Chem., Vol 78, pp 12726-12734 (2013). This compound is also known as GSK2330672 and sometimes abbreviated as GSK672.

This compound is in clinical trial for the prophylaxix and/or treament of a cholestatic liver disease and the associated pruritis.

SUMMARY OF THE INVENTION

Briefly, in a first aspect, the present invention discloses an improved synthesis of the compound

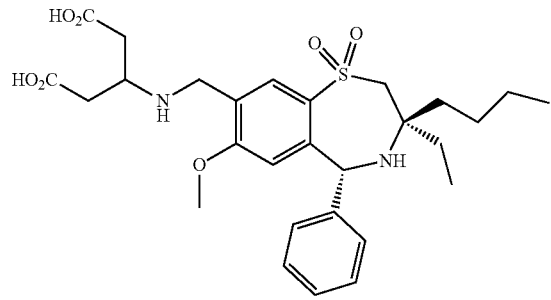 [SMILES: CCCC[C@]1(CC)CS(=O)(=O)c2cc(CNC(CC(=O)O)CC(=O)O)c(OC)cc2[C@@H](c2ccccc2)N1]

comprising the step of preparation of intermediate A, (R)-2-butyl-2-ethyloxirane

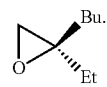

A

Briefly, in a second aspect, the present invention discloses an improved synthesis of the compound

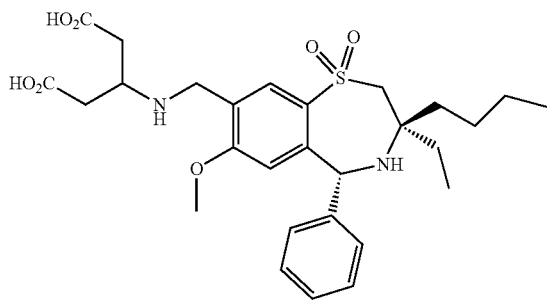 [SMILES: CCCC[C@]1(CC)CS(=O)(=O)c2cc(CNC(CC(=O)O)CC(=O)O)c(OC)cc2[C@@H](c2ccccc2)N1]

comprising the step of preparation of intermediate H depicted below

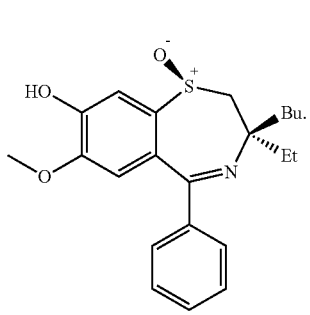

H

In another aspect the present invention provides a tablet comprising the compound GSK2330672.

In another aspect the present invention provides a method for treating a cholestatic liver disease and/or the associated pruritis, compising administration of the tablet of the present invention.

DETAILED DESCRIPTION OF THE INVENTION

Preferably, the first aspect of the invention as described above, comprises the kinetic resolution of racemic 2-butyl-2-ethyloxirane using an epoxide hydrolase to afford (R)-2-butyl-2-ethyloxirane (compound A). Epoxide hydrolases capable of selectively hydrolyzing 2-butyl-2-methloxirane and other geminally disubstituted epoxides are known in the literature (Bala, N. and Chimni, S. S. *Tetrahedron: Asymmetry* 2010, 21, 2879.), but on screening a random selection of eight epoxide hydrolases, we were surprised to identify some hits that were capable of selectively hydrolyzing either enantiomer of the more symmetrical 2-butyl-2-ethyloxirane substrate which has not previously been reported. In particular, the epoxide hydrolase from *Agromyces mediolanus* ZJB12020301D: JX467176 was very effective, transforming a 300 g/L of racemic epoxide in 15 h to afford the desired product (R)-2-butyl-2-ethyloxirane in 20% isolated yield and greater than 98% ee (solution yield, 40%) following extractive workup and subsequent purification by distillation under reduced pressure.

2-butyl-2-ethyloxirane concentrations within the range of 300-330 g/L are rarely reported in the literature especially with respect to wild type enzymes and suggests that the enzyme is unusually active and stable. During optimisation experiments we discovered that higher loadings of 2-butyl-2-ethyloxirane led to decreased enantioselectivity, either affording product that does not meet specification or resulting in substantial yield loss due to the need to run the resolution to higher conversion. On the other hand too low 2-butyl-2-ethyloxirane concentration lead to high enantioselectivity but is unattractive to run on scale due to the high reaction volume.

Other parameters were also shown to influence the enzyme enantioselectivity/activity and were screened to identify the process optimal conditions: temperature, buffer, mixing rate, cosolvent influence (solvents tested: heptane, TBME, hexane, diethyl ether, toluene); reaction vessel (test tubes, falcon tubes 15, 50 mL, shake flasks, controlled laboratory reactors), reaction time.

The enzyme can be used in different forms: whole cells, lyophilised unclarified lysate, immobilised or lyophilised clarified lysate while the loading can be also reduced from 20% down to 5-8% leading to a slower reaction but unchanged enantioselectivity. Use of lyophilised clarified lysate has the particular advantage over cell paste in that it is less problematic and cheaper to store and transport and leads to easier downstream processing. Lyophilised lysate is also cheaper than immobilised enzyme which can sometimes be advantageous in negating the need to recycle Some variants of *Agromyces mediolanus* ZJB12020301D: JX467176, that were reported to afford improved enantioselectivity to towards epichlorohydrin (Xue, F.; Liu, Z.-Q.; Wan, N.-W.; Zhu H.-Q. and Zheng, Y.-G. *RSC Adv.*, 2015, 5, 31525.), were also prepared and tested. One of these variants N240D gave higher activity (up to 30% higher) and slightly higher enantioselectivity than the wild-type enzyme.

Epoxide hydrolase from *Agromyces mediolanus* ZJB12020301D: JX467176 is a member of the large α/β-hydrolase fold family (Xue, F.; Liu, Z.-Q.; Zou, S.-P.; Wan, N.-W.; Zhu, W.-Y.; Zhu, Q. and Zheng, Y.-G. *Process Biochemistry* 2014, 49 409-417). This class of epoxide hydrolase, where all members contain very similar 3D architecture, is well known to encompass a surprisingly diverse sequence range (Widersten, M.; Gurell, A. and Lindberg, D. *Biochim. Biophys. Acta*, 2010, 1800, 316). Given that a number of enantioselective epoxide hydrolase enzymes were identified from the small subset tested, it is obvious that a larger set of epoxide hydrolases would yield hits that are as, if more more, selective than the epoxide hydrolase from *Agromyces mediolanus* ZJB12020301D: JX467176 that has been identified. Given the increased activity and enantioselectivity of one of three variants of the epoxide hydrolase from *Agromyces mediolanus* ZJB12020301D: JX467176, that had been selected for epichlorohydrin resolution, it is also highly likely that directed evolution towards 2-butyl-2-methloxirane would yield further improved mutants.

Preferably, the first aspect of the invention as described above, further comprises the step of reacting (R)-2-butyl-2-ethyloxirane with 3-hydroxy-4-methoxythiophenol to produce the intermediate C

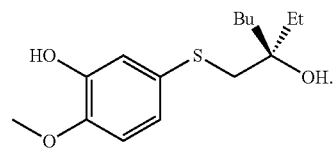

Preferably, the first aspect of the invention as described above, further comprises the step of converting intermediate C to the intermediate E shown below

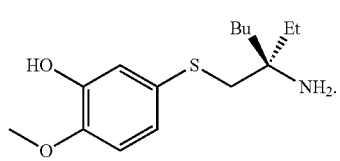

Preferably, the second aspect of the invention as described above, further comprises the step of converting intermediat H to intermediate I depicted below

I

Preferably the tablet and method of treatment of this invention comprise GSK2330672 prepared by a method of this invention.

In one aspect, the tablet of this invention further comprises filler, disintegrant, and lubricant. In one aspect the tablet of this invention comprises from 20 to 200 mg of GSK2330672. One example of a suitable tablet is a tablet comprising GSK2330672, microcrystalline cellulose, and magnesium stearate.

An illustrative synthetic scheme of how to prepare the IBAT inhibitor compound GSK672 is depicted in Scheme 1. Enzymatic resolution of (±)-2-butyl-ethyloxirane with epoxide hydrolase gave rise to (R)-2-butyl-ethyloxirane (A). Epoxide ring opening of (R)-2-butyl-ethyloxirane with thiophenol (B) and subsequent treatment of (R)-tertiary alcohol (C) with chloroacetonitrile under acidic conditions gave chloroacetamide (D), which was then converted to intermediate (E) by cleavage of the chloroacetamide with thiourea. Benzoylation of intermediate (E) with triflic acid and benzoyl chloride afforded intermediate (F). Cyclization of intermediate (F) followed by diastereoselective sulfoxidation of the sulfide to the chiral sulfoxide, subsequent imine reduction with sodium borohydride or borane provided intermediate (I), which was then converted to intermediate (J). Intermediate (J) was converted to the target compound using the methods disclosed in Patent publication WO 2011/137, 135.

Scheme 1

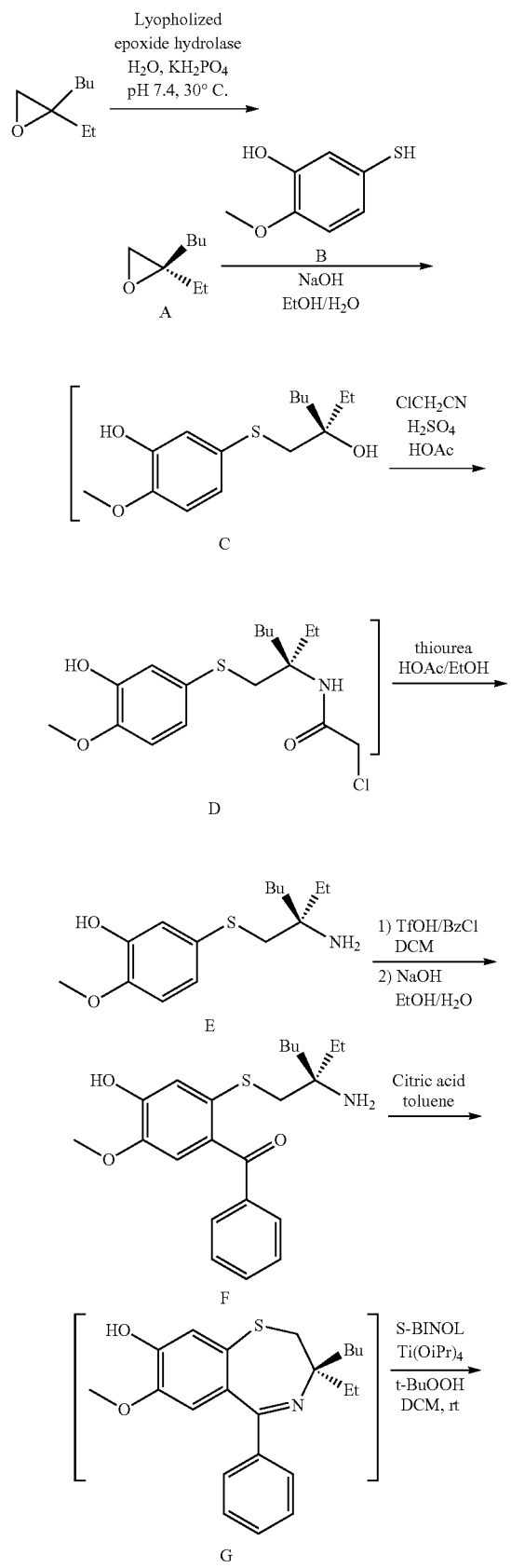

The present invention differs from the syntheses disclosed in WO 2011/137,135, *J. Med. Chem,* 2013, 56, 5094, *J. Org. Chem.* 2013, 78, 12726 and WO 2016020785 in that intermediates E and J in the present invention are prepared via new, stereoselective and more cost-efficient syntheses.

Abbreviations

Bz Benzoyl
TfOH Trifluoromethanesulfonic acid
BzCl Benzoyl chloride
S-BINOL (S)-(−)-1,1'-Bi(2-naphthol)
Ti(OiPr)4 Titanium isopropoxide
t-BuOOH tert-Butyl hydroperoxide
DCM Dichloromethane
NaBH₄ Sodium borohydride
MeOH Methanol mCPBA meta-Chloroperoxybenzoic acid
TFA Trifluoroacetic acid
MTBE Methyl t-butyl ether Intermediate A: (R)-2-butyl-2-ethyloxirane

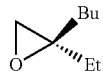

A

Note: 1 wt is defined as the weight of (±)-2-butyl-2-ethyloxirane charged to the reactor in grams. All other weights, volumes and equivalents given are calculated relative to this figure.

Lyopholized epoxide hydrolase enzyme from clarified lysate (20 wt %) was charged to the reaction vessel. Potassium phosphate buffer adjusted to pH 7.4 (100 mM, 1.4 vol) was then charged to the same reaction vessel and the agitation adjusted. The reaction was started by the addition of racemic 2-butyl-2-ethyloxirane (22.6 g, 176.3 mmol, 1 wt). The reaction mixture was stirred at 30° C. The reaction was monitored by chiral GC until the enantiomeric excess (ee) of (R)-2-butyl-2-ethyloxirane reached a value ≥95% (R) (typically conversion is around ≥62±2% over a 15 hr time period). The reaction was quenched by adding ethyl acetate (2.4 vol). The resultant biphasic solution was then filtered over Celite. Additional ethyl acetate (1.2 vol) was used to wash the celite cake. The layers were then separated. The aqueous layer was discarded. The organic layer was washed with brine (1.2 vol). The organic layer was then concentrated by distillation under reduced pressure to afford a neat mixture of the desired epoxide (R)-2-butyl-2-ethyloxirane and diol by-product (S)-2-ethylhexane-1,2-diol. The mixture was distilled at 90° C. and 20±5 mbar to give the desired epoxide (R)-2-butyl-2-ethyloxirane (4.58 g, 20% yield, 99.2% purity, 95% ee). $^1$H NMR (400 MHz, CDCl$_3$) δ2.61 (d, J=4.9 Hz, 1H), 2.59 (d, J=4.9 Hz, 1H), 1.72-1.46 (m, 4H), 1.42-1.26 (m, 4H), 0.99-0.87 (m, 6H). $^{13}$C NMR (125 MHz, CDCl$_3$) δ60.2, 52.2, 33.7, 27.0, 26.9, 22.9, 14.0, 8.9.

Intermediate E: (R)-5-((2-amino-2-ethylhexyl)thio)-2-methoxyphenol

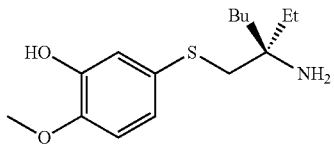

E

Under nitrogen protection, a reaction vessel was charged with 3-hydroxy-4-methoxythiophenol (564 mg, 3.61 mmol), (R)-2-butyl-2-ethyloxirane (509 mg, 3.97 mmol) and EtOH (3.4 mL). The mixture was treated with a solution of NaOH (318 mg, 7.94 mmol) in water (2.3 mL). The mixture was stirred at ambient temperature for 20 h. The mixture was treated with toluene (4 mL) and stirred for 2 min. The layers were separated and the organic layer was discarded. The aqueous layer was neutralized with 2N HCl and extracted with toluene. The extract was washed successively with saturated aqueous Na$_2$CO$_3$ solution and water, concentrated in vacuo to give intermediate C as an oil. The oil intermediate C was dissolved in chloroacetonitrile (5.5 mL) and HOAc (2 mL). The mixture was cooled to 0° C. H$_2$SO$_4$ (0.96 mL, 18.05 mmol, pre-diluted with 0.33 mL of water) was added at a rate maintaining the temperature below 5° C. After stirred at below 10° C. for 0.5 h, the reaction mixture was treated with water, extracted with MTBE. The extract was washed with saturated aqueous NaHCO$_3$ and concentrated in vacuo to give intermediate D as an oil. The oil intermediate D was then dissolved in EOH (9.1 mL) and treated with HOAc (1.8 mL) and thiourea (0.412 g, 5.42 mmol). The mixture was heated at reflux until completion, and then cooled to ambient temperature. The solids were removed by filtration The filtrate was concentrated in vacuo to give an oil. The oil was treated with EtOAc, washed successively with saturated aqueous Na$_2$CO$_3$ solution and water, and then concentrated in vacuo to give intermediate E (851 mg, 83% yield over 3 steps, 79% purity) as an oil. 425 mg of the intermediate E was further purified by silica gel chromatography to give intermediate E (223 mg, 100% purity, 94.8% ee). $^1$H NMR (400 MHz, CDCl$_3$) δ6.94 (d, J=2.2 Hz, 1H), 6.85 (dd, J=8.4, 2.2 Hz, 1H), 6.67 (d, J=8.4 Hz, 1H), 5.23 (s, 1H), 3.78 (s, 3H), 2.87 (s, 2H), 1.46-1.28 (m, 4H), 1.25-1.05 (m, 4H), 0.81 (t, J=6.9 Hz, 3H), 0.76 (t, J=7.45 Hz, 3H). $^{13}$C NMR (125 MHz, CDCl$_3$) δ146.0, 129.1, 122.9, 117.7, 111.2, 56.0, 54.8, 47.5, 38.6, 31.8, 25.8, 23.3, 14.1, 8.0.

Intermediate H: (1S,3R)-3-butyl-3-ethyl-8-hydroxy-7-methoxy-5-phenyl-2,3-dihydrobenzo[f][1,4]thiazepine 1-oxide

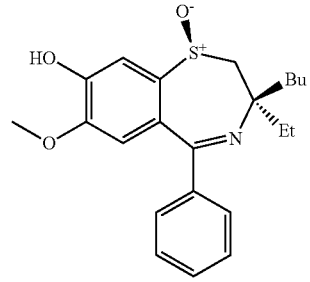

H (S)-(−)-1,1'-Bi(2-napthol) (387 mg, 1.353 mmol, 1 equiv) was charged into a 15 mL RBF. A magnetic stirbar was added and the flask was sealed with a septum and flushed with nitrogen for 10 minutes. Dichloromethane (5 ml, 10 vol) was added followed by the dropwise addition of titanium tetraisopropoxide (0.200 mL, 0.677 mmol, 0.5 equiv), at which time a deep red color change was observed. Water (49 μL, 2.71 mmol, 2 equiv) was added and the reaction was stirred for 15 minutes. The septum was removed and intermediate G (500 mg, 1.353 mmol, 1 equiv) was added in one portion. The septum was replaced and the reaction was stirred for 15 minutes, after which time tert-butyl hydroperoxide (5.0-6.0 M in decane, 0.284 mL, ~1.42 mmol, ~1.05 equiv) was added dropwise. The reaction was stirred at ambient temperature for 2.5 hours with monitoring by fast HPLC, after which time another 27 μL of tert-butyl hydroperoxide was added. After another 1 h, the reaction was deemed complete by fast HPLC and quenched by the addtion of sat. sodium sulfite (1 mL, 2 vol). The reaction was transferred to a separatory funnel and diluted with a small amount of water and dichloromethane. The organic layer was separated, dried over magnesium sulfate, concentrated and directly purified by column chromatography (gradient of 20-100% EtOAc in hexanes) to yield 419 mg of intermediate H as an orange solid in 90% PAR and 80% yield as a single diastereomer. $^1$H NMR (400 MHz, CDCl$_3$) δ7.74 (s, 1H), 7.60-7.54 (m, 2H), 7.46-7.40 (m, 1H), 7.39-7.33 (m, 2H), 6.67 (s, 1H), 3.81 (d, J=12.4 Hz, 1H), 3.79 (s, 3H), 3.30 (d, J=12.4 Hz, 1H), 2.07-1.84 (m, 2H), 1.24-0.94 (m, 9H), 0.74 (t, J=6.6 Hz, 3H). $^{13}$C NMR (125 MHz, CDCl$_3$) δ163.4, 149.0, 148.9, 140.5, 135.7, 130.4, 129.1, 128.2, 123.2, 112.3, 109.1, 70.6, 60.7, 56.5, 38.2, 37.2, 25.4, 22.9, 13.9, 8.6.

Intermediate J: (3R,5R)-3-butyl-3-ethyl-8-hydroxy-7-methoxy-5-phenyl-2,3,4,5-tetrahydrobenzo[f][1,4]thiazepine 1,1-dioxide

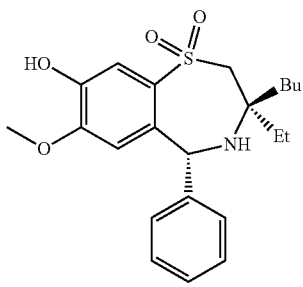

J

Intermediate H (100 mg, 0.259 mmol) was dissolved in dichloromethane (370 µL, 3.7 vol) and then methanol (830 µL, 8.3 vol) was added. The reaction was cooled in an ice bath and sodium borohydride (11.8 mg, 1.2 equiv) was added in one portion. Monitoring by fast HPLC showed the reaction to be complete within 10 minutes. The reation was quenched by the addition of water (0.5 mL, 5 vol). The reaction was transfered to a separatory funnel and diluted with a small amount of water and dichloromethane. The organic phase was split and washed with sat. NaHCO$_3$, brine and then dried over magnesium sulfate and concentrated to give intermediate I. Intermediate I was dissolved in dichloromethane (1 mL, 1 vol). The reaction was cooled in an ice bath and trifluoroacetic acid (21 µL, 1.05 equiv) was added. The reaction was stirred for 5 minutes and then mCPBA (77%, 64 mg, 1.1 equiv) was added in one portion and the reaction was removed from the ice bath. After 10 minutes, fast HPLC showed less than 5% PAR of starting material The reaction was stirred for another 10 minutes and then sat. NaHCO$_3$ (2.5 mL, 2.5 vol) and 1M NaSO$_3$ (2.5 mL, 2.5 vol) were added and the reaction was stirred for several minutes. The reaction was diluted with water and dichloromethane and the organic layer was separated and dried ove magnesium sulfate. The solution was concentrated and recrystallization attempted from TBME to give material of low purity. The solids and mother liqour were recombined and chromatograpahed (0-50% EtOAc in hexanes) to give 44 mg of intermediate J, ~97% PAR and 44% yield over 2 steps. $^1$H NMR (400 MHz, CDCl$_3$) δ7.65 (s, 1H), 7.46-7.35 (m, 4H), 7.35-7.28 (m, 1H), 6.15 (s, 1H), 6.02 (s, 1H), 3.58 (s, 3H), 3.41 (d, J=14.9 Hz, 1H), 3.05 (d, J=14.9 Hz, 1H), 2.22-2.09 (m, 1H), 1.89-1.77 (m, 1H), 1.57-1.39 (m, 2H), 1.35-1.06 (m, 4H), 0.88 (t, J=7.4 Hz, 3H), 0.83 (t, J=6.9 Hz, 3H). $^{13}$C NMR (125 MHz, CDCl$_3$) δ149.6, 143.9, 142.3, 138.5, 132.5, 128.5, 127.8, 127.3, 114.5, 110.8, 63.9, 57.4, 55.8, 55.2, 34.1, 31.2, 25.3, 22.9, 14.1, 7.6.

Treatment of a Cholestatic Liver Disease

A clinical study was carried out to investigate the safety, tolerability, and effect of repeat doses of GSK672 administration in patients with primary biliary cholangitis (PBC) and symptoms of pruritus. The results of this study have been summarized and published on clintrials.gov A phase 2 double-blind, randomised, placebo controlled, crossover trial in PBC patients with pruritus was conducted at two specialist PBC centres in the United Kingdom between March 2014 and November 2015. Subjects received oral GSK672 (45 to 90 mg) and placebo twice daily for 14 days in a crossover sequence.

The primary end point was safety [measured by clinical and laboratory assessments and adverse events (AEs)] and tolerability. Secondary end points were: i) changes in pruritus scores from baseline measured using a 0 to 10 numerical rating scale (NRS) completed twice daily and PBC-40 itch domain scores and 5-D itch scale and ii) changes in serum levels of total bile acids (TBA) and 7alpha-hydroxy-4-cholesten-3-one (C4). Serum levels of individual BA species, autotaxin (ATX) activity and FGF19 were measured at baseline and at the end of each treatment period.

21 patients (n=21, all Caucasians, 18 females, mean age 52.9±10.5 years) completed the study and were analysed. 68% were taking Ursodeoxycholic acid (UDCA) during the study period. No serious AEs were reported. Frequency of any AE was 81% (17/21) each during placebo and GSK672 periods. Diarrhoea (33% & 5%) and headache (29% & 33%) were the most frequent AE associated with GSK672 and placebo respectively. GSK672 demonstrated 71% response rate and showed significant reduction in itch intensity as measured by NRS [−1.58 (95% CI: −2.48 to −0.68)], PBC-40 itch domain [−0.59 (95% CI: −0.94 to −0.24)] and 5-D itch [−4.55 (95% CI: −6.60 to −2.49)]. Baseline values of serum TBA levels (48.64±68.77 µM) decreased after GSK672 treatment (25.15±23.85 µM, p=0.15) but not after placebo (50.29±55.96 µM, p=0.93). GSK672 significantly reduced serum levels of taurocholate (3.47±7.15 vs. 0.31±0.74 µM, p=0.0004), glycocholate (4.44±7.43 vs. 0.9±1.21 µM, p=0.0013), and taurochenodeoxycholate (3.68±7.50 vs. 0.8±1.46 µM, p=0.002). Following GSK672, serum ATX activity (8.25±4.17 vs. 6.95±2.62 nMol/ml/min, p=0.006) and serum FGF19 levels (162.9±107.5 vs. 50.66±47.31 pg/mL, p<0.0001) were lower and serum levels of deoxycholate (3.1±0.55 vs. 3.39±0.64 µM, p=0.009) and C4 (13.13±10.04 vs.35.2±25.32 ng/ml, p=0.0006) were higher.

Study Conclusion

In summary, two weeks of oral twice daily GSK2330672 was well tolerated and reduced itch intensity in a high proportion of PBC patients with pruritus. The substantial reduction in serum total and conjugated primary bile acids and FGF19 levels and increase in serum C4 levels are consistent with the mechanism of action of IBAT inhibition. These results support further investigation of GSK2330672 as a potential treatment for cholestatic pruritus.

In addition to the above PBC study, GSK2330672 has been administered in other studies. GSK2330672 is an inhibitor of the ileal bile acid transporter (IBAT) that was first administered to humans in June 2011. It is being evaluated as a treatment for liver disease associated with cholestasis. Previous development for treatment of type 2 diabetes (T2D) was terminated after completion of two Phase II studies in T2D subjects taking background metformin. As of 3 Jun. 2016 preliminary results are available for one Phase II repeat dose study conducted in subjects with pruritus due to Primary Biliary Cholangitis (PBC). Overall data are available from 132 subjects exposed to GSK2330672, including 59 healthy subjects, 52 T2D subjects, and 21 PBC pruritus subjects. Of these, the maximum dose of 90 mg BID was administered to 51 subjects, including 6 healthy patients (1 day), 24 T2D patients (up to 14 days), and 21 PBC pruritus subjects (up to 14 days).

Among these studies three non-fatal serious adverse events (SAEs) were reported. One healthy subject experienced a bleeding thrombosed external haemorrhoid after a single 30 mg dose. Among T2D subjects, one experienced acute cholecystitis and one experienced atrial flutter/fibrillation. No SAEs were reported from the PBC pruritus subjects. No deaths or pregnancies were reported from any study. Gastrointestinal symptoms related to the targeted site of action were the most commonly reported adverse events (AEs) associated with GSK2330672 and included diarrhea, abdominal pain and bowel movement irregularity. Trace positive fecal occult blood tests were also observed in a minority of participants, with no clinical sequelae. There were no clinically significant patterns of abnormal vital sign measurements, electrocardiogram (ECG) changes, spirometry parameters or clinical laboratory findings observed in healthy subjects, T2D patients, or PBC pruritus patients.

In summary, administration of the IBAT inhibitor, GSK2330672, did not result in any findings during safety monitoring that would preclude conduct of planned short-term clinical trials in patient populations with T2D or primary biliary cholangitis. However, the high frequency of diarrhea AEs among T2D subjects taking metformin 850 mg BID contributed to the decision to terminate development of this condition.

Because the pharmacological target of GSK2330672 is located on the brush border of enterocytes in the intestinal lumen, the molecule was designed to have low permeability and high polar surface area to limit absorption into the portal or systemic circulation. Blood samples were obtained at frequent intervals after administration of GSK2330672 for assays of plasma drug concentrations. The majority of measurements were below the lower limit of quantification for the assay (LLQ=1 ng/mL). The highest measurable concentration was 5.33 ng/ml obtained 2 hours post-dose in 1 subject, confirming limited absorption into the systemic circulation.

Oral administration of GSK2330672 at doses ≥0 mg clearly inhibited the ileal bile acid transporter. For healthy subjects, single doses in this range significantly increased fecal bile acid excretion measured over the subsequent 48 hours. Repeated doses suppressed both fasting and postprandial bile acid concentrations measured on Day 1 and Day 10 of dosing. The anticipated adaptive response to inhibited bile acid reabsorption, upregulation of hepatic bile acid synthesis, was estimated by measuring serum concentrations of 7-alpha-hydroxy-4-cholesten-3-one (C4). With repeated doses of GSK2330672, serum C4 concentrations increased up to 10-fold after ten days of dosing.

For the T2D subjects who completed the full 7-day treatment period with GSK2330672 added to metformin in Study 200185, repeated doses of GSK2330672 increased on Day 3 from 45 to 90 mg BID significantly decreased serum total bile acid concentrations and increased C4 concentrations. Furthermore, GSK2330672 significantly reduced plasma glucose and low-density lipoprotein cholesterol (LDL-C) from baseline when compared with placebo. For glucose weighted mean area under the curve for the 24 hours after the morning dose [AUC(0-24 h)], the decrease was statistically significant [least square mean difference from placebo (95% confidence interval): −34.76 mg/dL (−54.67, −14.85)]. GSK2330672 elicited a 41.7% mean reduction in fasting LDL-C from baseline, compared to a 3.5% mean increase in the same time period for the placebo group. Fasting serum triglycerides were relatively stable in the GSK2330672 group and on average decreased −16.0% in the placebo group.

For T2D subjects who completed the 14-day treatment period with GSK2330672 added to metformin in Study 201351, repeated doses of GSK2330672 from 10 mg to 90 mg BID reduced circulating prandial glucose concentrations at all doses compared to placebo and sitagliptin over 14 hours post-dose. The circulating concentrations of serum C4 were increased over 14 hours post-dose by GSK2330672 at all doses compared to placebo and sitagliptin; while C4 concentrations for the 10 mg, 20 mg, 30 mg and 60 mg of GSK2330672 groups appear to have reached a plateau by Day 7, this was not the case for the 90 mg group in which the Day 14 values were greater than those at Day 7.

In a two-week dose-ranging study among T2D subjects, GSK2330672 significantly reduced plasma glucose and low-density lipoprotein cholesterol (LDL-C) from baseline when compared with placebo or sitagliptin. Reductions in fasting plasma glucose were greater in GSK2330672 30 mg, 60 mg, and 90 mg groups on Day 7 and Day 14 compared to placebo and sitagliptin groups. For the 90 mg BID group, a statistically significant reduction was observed for glucose weighted mean area under the curve for the 24 hours after the morning dose [AUC(0-24 h)]: least square mean difference from placebo (95% confidence interval) was −34.76 (−54.67, −14.85) mg/dL. The reduction in fasting plasma insulin was variable at Day 14 across the GSK2330672 doses with no dose-response, but the greatest reduction was observed in the GSK2330672 90 mg group compared to the placebo: (LS mean difference from placebo [95% CI]: −17.61 pmol/L [−33.73, −1.48]). Reductions in fasting serum apoB, total cholesterol, direct LDL cholesterol and non-HDL cholesterol concentrations from baseline were observed in all the GSK2330672 dose groups, compared to placebo and sitagliptin, with no apparent dose-response. The greatest mean reduction was observed in the GSK2330672 60 mg group (LS mean change from baseline (expressed as a ratio) difference from placebo [95% CI]: 0.74 (0.66, 0.82). There was a trend for an increase in triglyceride concentrations in all the GSK2330672 dose groups, and there were no clinically meaningful changes in HDL cholesterol in any dose group.

In a randomized placebo controlled 14 day cross-over study in 22 subjects with PBC pruritus (Study 117213), GSK2330672 at 90 mg BD resulted in a statistically significant decrease in pruritus severity compared to placebo as evidenced by 3 different rating scales (10 point numerical rating scale, 5D Itch Scale, and PBC-40). Reduction of pruritus severity occurred within the first week of GSK2330672, continued to decrease through 2 weeks of treatment and returned towards baseline upon blinded switch to placebo. Decreases in fatigue, sleep disturbance and overall disability were also noted upon GSK2330672 administration compared to placebo. Statistically significant target engagement by GSK2330672 was demonstrated by approximately 50% decrease in concentration of serum total bile acids, and 3 fold increase in serum C-4. GSK2330672 was minimally absorbed as evidenced by detection in isolated samples in a small portion of subjects (8 out of 21). No GSK2330672-related metabolites were detected in plasma or urine. Parent compound (GSK2330672) was the only drug related material observed in the urine, and the concentration was low and not observed in all subjects. GSK2330672 did not inhibit the absorption of ursodeoxycholic acid (UDCA), although there was a statistically significant reduction in the pharmacokinetics of the UDCA conjugates, glycoursodeoxycholic acid (GUDCA) and tauroursodeoxycholic acid (TUDCA). Of note, plasma concentrations of TUDCA and GUDCA were still at levels associated with clinical efficacy in published studies of UDCA therapy for PBC. Dilger K, Hohenester S, Winkler Budenhofer U, Bastiaansen B, Schapp F, Rust C, Beuers U. Effect of ursodeoxycholic acid on bile acid profiles and intestinal detoxification machinery in primary biliary cirrhosis and health. *Journal of Hepatology.* 2012; 57:133-40.

What is claimed is:

1. A method for synthesis of the compound GSK2330672:

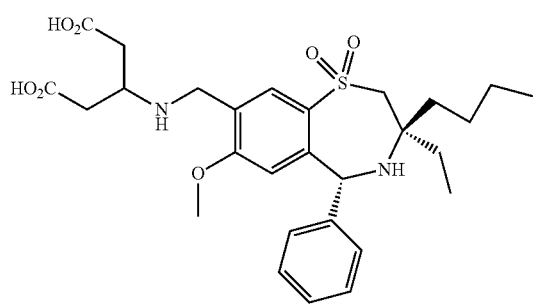

GSK2330672 comprising the step of preparation of intermediate A, (R)-2-butyl-2-ethyloxirane

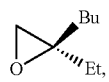

followed by conversion of (R)-2-butyl-2-ethyloxirane through one or more steps to GSK2330672.

2. The method of claim 1 further comprising the step of reacting (R)-2-butyl-2-ethyloxirane with 3-hydroxy-4-methoxythiophenol to produce intermediate C:

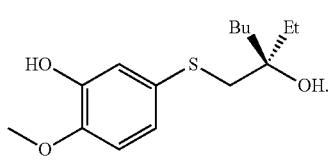

3. The method of claim 2 further comprising the step of converting intermediate C via a stereoselective Ritter reaction to intermediate E:

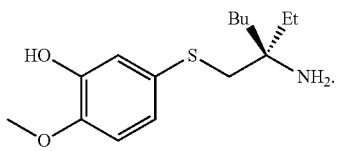

4. A method for synthesis of the compound GSK2330672:

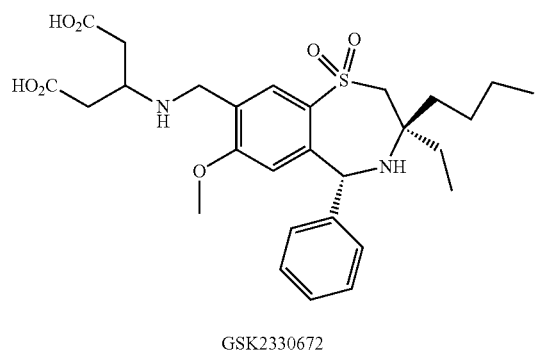 [SMILES: CCCC[C@]1(CC)CS(=O)(=O)c2cc(CNC(CC(=O)O)CC(=O)O)c(OC)cc2[C@@H](c2ccccc2)N1]

GSK2330672 comprising the step of preparation of intermediate H:

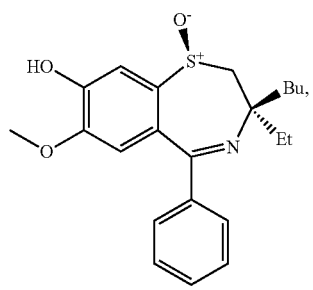

followed by conversion of intermediate H through one or more steps to GSK2330672.

5. The method of claim 1 further comprising the step of preparing intermediate H:

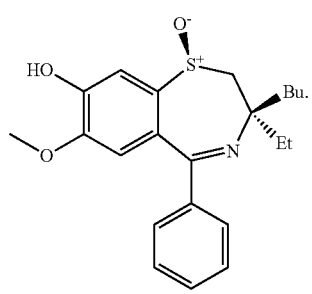

6. The method of claim 4 further comprising the step of converting intermediate H to intermediate I:

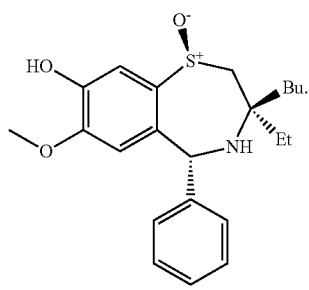

7. The method of claim 6 further comprising the step of converting intermediate I to intermediate J:

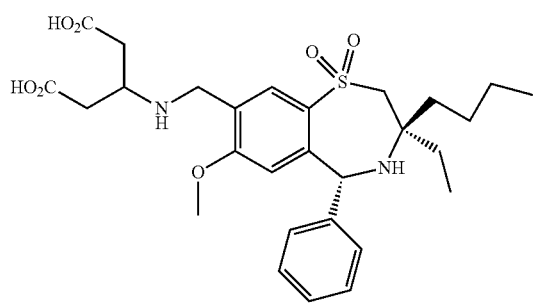

8. The method of claim 1 wherein said compound A is made by the kinetic resolution of racemic 2-butyl-2-ethyl-oxirane with an epoxide hydrolase.

9. The method of claim 8 wherein said epoxide hydrolase is from *Agromyces mediolanus* ZJB12020301D: JX467176.

10. The method of claim 9 wherein said epoxide hydrolase is a mutant N240D of the epoxide hydrolase from Agromyces mediolanus ZJB12020301D: JX467176.

11. The method of claim 8 wherein the concentration of said racemic 2-butyl-2-ethyloxirane is from 200-330 g/L.

12. A method for synthesizing the compound GSK2330672:

comprising the steps of:
preparing intermediate A, (R) -2 -butyl-2 -ethyloxirane

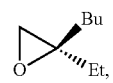

by kinetic resolution of racemic 2-butyl-2-ethyloxirane with an epoxide hydrolase;
reacting (R)-2-butyl-2-ethyloxirane with 3-hydroxy-4-methoxythiophenol to produce intermediate C:

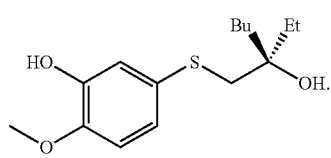

converting intermediate C via a stereoselective Ritter reaction to intermediate E:

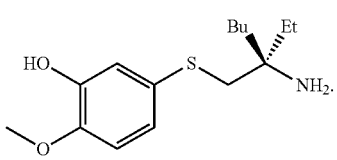

benzoylating intermediate E to produce intermediate F:

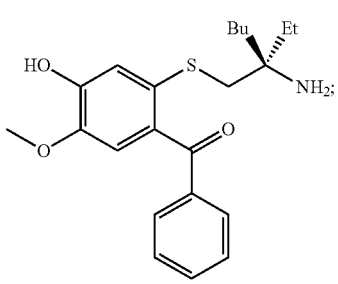

cyclizing intermediate F followed by diastereoselective sulfoxidation to produce intermediate H:

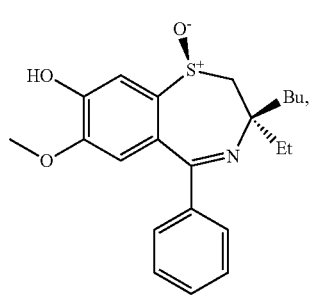

reducing the imine of intermediate H to produce intermediate I:

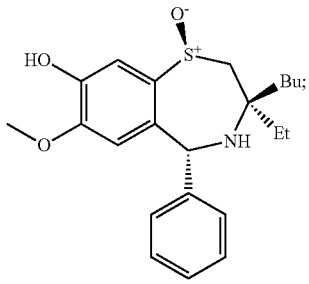

and
sulfoxidizing intermediate I to produce intermediate J:

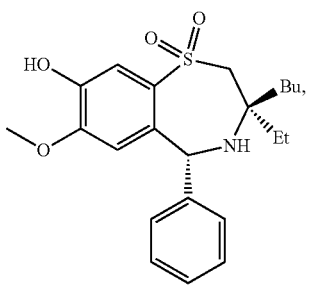

followed by conversion of intermediate J through one or more steps to GSK2330672.

13. The method of claim 12 wherein the epoxide hydrolase is from *Agromyces mediolanus* ZJB1202030ID: JX467176.

14. The method of claim 13 wherein the epoxide hydrolase is a mutant N240D of the epoxide hydrolase from Agromyces mediolanus ZJB1202030ID: JX467176.

15. The method of claim 12 wherein the concentration of the racemic 2-butyl-2-ethyloxirane is from 200-330 g/L.

16. The method of claim 12 wherein the epoxide hydrolase is used in a form selected from the group consisting of whole cell, lyophilized unclarified lysate, lyophilized clarified lysate, and immobilized clarified lysate.

17. The method of claim 16 wherein the epoxide hydrolase used is in the lyophilized clarified lysate form.

18. The method of claim 12 wherein the step of benzoylating intermediate E to produce intermediate F includes triflic acid and benzoyl chloride.

19. The method of claim 1 wherein the epoxide hydrolase is used in a form selected from the group consisting of whole cell, lyophilized unclarified lysate, lyophilized clarified lysate, and immobilized clarified lysate.

20. The method of claim 19 wherein the epoxide hydrolase used is in the lyophilized clarified lysate form.

21. The method of claim 3 further comprising the step of benzoylating intermediate E using triflic acid and benzoyl chloride to produce intermediate F:

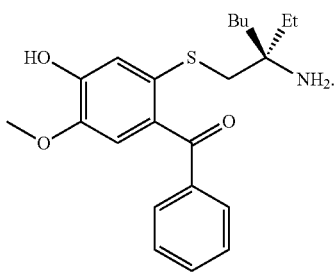

* * * * *